US008107060B2

(12) United States Patent
Hebrank et al.

(10) Patent No.: US 8,107,060 B2
(45) Date of Patent: *Jan. 31, 2012

(54) METHODS AND APPARATUS FOR CANDLING EGGS VIA EMBRYO HEARTBEAT DETECTION

(75) Inventors: John H. Hebrank, Durham, NC (US); Daniel L. Kennedy, Wake Forest, NC (US)

(73) Assignee: Embrex, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/947,225

(22) Filed: Nov. 29, 2007

(65) Prior Publication Data
US 2009/0091743 A1 Apr. 9, 2009

Related U.S. Application Data

(63) Continuation-in-part of application No. 11/867,996, filed on Oct. 5, 2007, now abandoned.

(51) Int. Cl.
*A01K 43/00* (2006.01)
*G01N 33/08* (2006.01)
(52) U.S. Cl. ......................................................... 356/53
(58) Field of Classification Search .............. 356/52–68; 119/6.8; 209/510–516
See application file for complete search history.

(56) References Cited

U.S. PATENT DOCUMENTS

| 2,823,800 | A | * | 2/1958 | Bliss | 209/511 |
| 3,540,824 | A | | 11/1970 | Fonda et al. | |
| 3,910,701 | A | * | 10/1975 | Henderson et al. | 356/39 |
| 4,161,366 | A | * | 7/1979 | Bol et al. | 356/56 |
| 4,205,752 | A | * | 6/1980 | Malvick et al. | 209/564 |
| 5,646,722 | A | * | 7/1997 | van der Schoot | 356/53 |
| 5,845,002 | A | * | 12/1998 | Heck et al. | 382/110 |
| 6,014,222 | A | * | 1/2000 | Borggaard et al. | 356/419 |
| 6,750,954 | B2 | | 6/2004 | Hebrank et al. | |
| 6,844,931 | B2 | * | 1/2005 | Ehbets | 356/328 |

(Continued)

FOREIGN PATENT DOCUMENTS
JP 06-043093 2/1994
(Continued)

OTHER PUBLICATIONS

PCT International Search Report, date of mailing Apr. 8, 2009; International Publication/Application No. WO2009/044243 / PCT/IB2008/002481.

(Continued)

*Primary Examiner* — Gordon Stock, Jr.
(74) *Attorney, Agent, or Firm* — Brandon Boss; Scott C. Mayhew (57) ABSTRACT

An apparatus for candling eggs includes a waterproof housing having a free end, a light source configured to emit visible light from the housing free end and illuminate an egg positioned adjacent to the housing free end, and a photodetector that generates an output signal corresponding to intensity of light from the light source leaving the egg. The photodetector is shielded from external light and from direct light from the light source. The light source and photodetector are disposed within the waterproof housing, and a replaceable bumper is removably secured to the housing free end. The bumper is configured to engage an egg in contacting relation therewith, and to shield the photodetector from external light and from direct light from the light source. A processor processes output signals from the photodetector to identify cyclical variations in light intensity and/or non-cyclical variations in light intensity.

28 Claims, 8 Drawing Sheets

U.S. PATENT DOCUMENTS

| | | | |
|---|---|---|---|
| 6,850,316 B2 * | 2/2005 | Hebrank | 356/53 |
| 6,860,225 B2 * | 3/2005 | Hebrank | 119/6.8 |
| 7,154,594 B2 | 12/2006 | Reeves et al. | |
| 7,167,579 B2 * | 1/2007 | Taniguchi | 382/110 |
| 7,173,246 B2 * | 2/2007 | Benedetti et al. | 250/358.1 |
| 7,289,196 B2 | 10/2007 | Reeves et al. | |
| 7,573,567 B2 | 8/2009 | Hershtik | |
| 2004/0107912 A1 * | 6/2004 | Hebrank | 119/6.8 |
| 2004/0130720 A1 * | 7/2004 | Maeda et al. | 356/419 |
| 2005/0206876 A1 * | 9/2005 | Reeves et al. | 356/52 |

FOREIGN PATENT DOCUMENTS

| | | |
|---|---|---|
| JP | 09-127096 | 5/1997 |
| JP | 2001-318048 | 11/2001 |
| JP | 2004184113 A * | 7/2004 |
| NL | 1013375 C2 * | 4/2001 |
| WO | WO 0036411 A1 * | 6/2000 |

OTHER PUBLICATIONS

PCT Written Opinion, date of mailing Apr. 8, 2009; International Application No. PCT/IB2008/002481.

* cited by examiner

METHODS AND APPARATUS FOR CANDLING EGGS VIA EMBRYO HEARTBEAT DETECTION

RELATED APPLICATION

This application is a continuation-in-part application of U.S. patent application Ser. No. 11/867,996, filed Oct. 5, 2007 now abandoned, the disclosure of which is incorporated herein by reference in its entirety as if set forth fully herein.

FIELD OF THE INVENTION

The present invention relates generally to eggs and, more particularly, to methods and apparatus for candling eggs.

BACKGROUND

Discrimination between poultry eggs on the basis of some observable quality is a well-known and long-used practice in the poultry industry. "Candling" is a common name for one such technique, a term which has its roots in the original practice of inspecting an egg using the light from a candle. As is known to those familiar with eggs, although egg shells appear opaque under most lighting conditions, they are in reality somewhat translucent, and when placed in front of direct light, the contents of the egg can be observed.

Eggs which are to be hatched to live poultry are typically candled during embryonic development to identify clear, rotted, and dead eggs (collectively referred to herein as "non-live eggs"). Non-live eggs are removed from incubation to increase available incubator space. In many instances it is desirable to introduce a substance, via in ovo injection, into a live egg prior to hatch. Injections of various substances into avian eggs are employed in the commercial poultry industry to decrease post-hatch mortality rates or increase the growth rates of the hatched bird. Examples of substances that have been used for, or proposed for, in ovo injection include vaccines, antibiotics and vitamins. In ovo treatment substances and methods are described in U.S. Pat. No. 4,458,630 to Sharma et al. and U.S. Pat. No. 5,028,421 to Fredericksen et al.

In ovo injections of substances typically occur by piercing an egg shell to create a hole therethrough (e.g., using a punch, drill, etc.), extending an injection needle through the hole and into the interior of the egg (and in some cases into the avian embryo contained therein), and injecting one or more treatment substances through the needle. An example of an injection device is disclosed in U.S. Pat. No. 4,681,063 to Hebrank. This device positions an egg and an injection needle in a fixed relationship to each other, and is designed for the high-speed automated injection of a plurality of eggs. The selection of both the site and time of injection treatment can also impact the effectiveness of the injected substance, as well as the mortality rate of the injected eggs or treated embryos. See, for example, U.S. Pat. No. 4,458,630 to Sharma et al., U.S. Pat. No. 4,681,063 to Hebrank, and U.S. Pat. No. 5,158,038 to Sheeks et al.

In commercial poultry production, typically only about 60% to 90% of commercial broiler eggs hatch. Eggs that do not hatch include eggs that were not fertilized, as well as fertilized eggs that have died. Infertile eggs may comprise from about 5% up to about 25% of all eggs in a set. Due to the number of non-live eggs encountered in commercial poultry production, the increasing use of automated methods for in ovo injection, and the cost of treatment substances, an automated method for identifying live eggs and selectively injecting only live eggs, is desirable.

There are other applications where it is important to be able to identify live and non-live eggs. One of these applications is the cultivation and harvesting of vaccines in live eggs (referred to as "vaccine production eggs"). For example, human flu vaccine production is accomplished by injecting seed virus into a chicken egg at about day eleven of embryonic development (Day-11 egg), allowing the virus to grow for about two days, euthanizing the embryo by cooling the egg, and then harvesting the amniotic fluid from the egg. Typically, eggs are candled before injection of a seed virus to facilitate removal of non-live eggs. Vaccine production eggs may be candled one or more days prior to injection of a seed virus therein. Identification of live eggs in vaccine production is important because it is desirable to prevent seed vaccine from being wasted in non-live eggs, to reduce costs associated with transporting and disposing of non-live eggs, and to reduce the possibility of contamination from non-live eggs.

U.S. Pat. No. 3,616,262 to Coady et al. discloses a conveying apparatus for eggs that includes a candling station and an inoculation station. At the candling station, light is projected through the eggs and assessed by a human operator, who marks any eggs considered non-live. Non-live eggs are manually removed before the eggs are conveyed to the inoculating station.

U.S. Pat. Nos. 4,955,728 and 4,914,672, both to Hebrank, describe a candling apparatus that uses infrared detectors and the infrared radiation emitted from an egg to distinguish live from infertile eggs. U.S. Pat. No. 5,745,228 to Hebrank et al. describes a candling apparatus that includes a photodetector and a photoemitter that are configured to be positioned on opposite sides of an egg. Light is generated in short bursts from each photoemitter and the corresponding photodetector monitors while its corresponding photoemitter is operational. A flat of eggs is continuously "scanned" as it moves through the candling apparatus with each detector-source pair active while at least adjacent, and preferably all other, pairs are quiescent.

Embryo heartbeat (pulse) detection methods are known that can detect live eggs with a high degree of accuracy. For example, U.S. Pat. No. 6,860,225 to Hebrank describes candling methods and apparatus wherein cyclical variation in light intensity indicates the existence of an embryo pulse. U.S. Pat. No. 5,173,737 to Mitchell describes a method of determining whether an egg contains a live embryo by directing light into an egg to stimulate embryo movement, and then measuring resulting embryo movement.

Electrical components utilized in embryo heartbeat detection technology can be sensitive to the environment. Unfortunately, egg candling is typically performed in wet, harsh environments that can potentially affect sensitive electronic components.

SUMMARY

In view of the above discussion, egg candling methods and apparatus are provided that can be utilized in the wet, harsh environments of a hatchery and other poultry facilities. According to some embodiments of the present invention, an apparatus for candling eggs includes a waterproof housing having a free end; at least one light source configured to emit visible light from the housing free end and illuminate an egg positioned adjacent to the housing free end; and a photodetector at the housing free end that generates an output signal corresponding to intensity of light from the at least one light source leaving the egg. The photodetector is shielded from external light and from direct light from the at least one light source. The at least one light source is disposed within the housing and emits visible light within a range of between 600 nm and 740 nm through a transparent window. The photodetector is disposed within the housing and receives light leaving an egg through the transparent window.

In some embodiments, the at least one light source emits visible light within a range of between 610 nm and 720 nm. In some embodiments, the at least one light source is a light emitting diode (LED) that is configured to emit visible light with a peak intensity at one of the following wavelengths: 625 nm, 639 nm, 660 nm, and 695 nm.

A replaceable bumper is removably secured to the housing free end and is configured to engage an egg in contacting relation therewith. The bumper is configured to shield the photodetector from external light and from direct light from the at least one light source. In some embodiments, a processor is disposed within the housing. The processor processes output signals from the photodetector to identify cyclical variations in light intensity, wherein a cyclical variation in light intensity indicates the existence of an embryo pulse. In some embodiments, the processor may also process output signals from the photodetector to identify non-cyclical variations in light intensity, wherein non-cyclical variations in light intensity indicate embryo movement.

According to other embodiments of the present invention, an apparatus for candling eggs includes a waterproof housing having a free end with a transparent window. A pair of light sources is disposed within the housing and each light source is configured to emit visible light within a range of between 600 nm and 740 nm from the housing free end through the window and illuminate an egg positioned adjacent to the housing free end. A photodetector is positioned within the housing at the free end between the pair of light sources and generates an output signal corresponding to the intensity of light from the light sources leaving the egg. The photodetector is shielded from external light and from direct light from the light sources via a replaceable bumper removably secured to the housing free end. A processor is disposed within the housing and is configured to process output signals from the photodetector to identify cyclical variations in light intensity, wherein a cyclical variation in light intensity indicates the existence of an embryo pulse. In some embodiments of the present invention, the processor processes output signals from the photodetector to identify non-cyclical variations in light intensity, wherein non-cyclical variations in light intensity indicate embryo movement.

According to further embodiments of the present invention, a method of candling eggs includes positioning an egg adjacent a free end of a detector tool, wherein the detector tool has at least one light source and a photodetector; illuminating the egg with visible light within a range of between 600 nm and 740 nm from the free end via the at least one light source; detecting intensity of light leaving the egg via the photodetector, wherein the photodetector is shielded from external light and from direct light from the at least one light source; generating an output signal that corresponds to detected light intensity; and processing the output signal to identify cyclical and/or non-cyclical variations in light intensity, wherein cyclical variations in light intensity indicate the existence of an embryo pulse, and wherein non-cyclical variations in light intensity indicate embryo movement. In some embodiments, illuminating the egg with light includes illuminating the egg with light from one or more selected portions of the spectrum such as, for example, the visible and/or infrared portions of the spectrum.

According to other embodiments of the present invention, an apparatus for candling eggs includes a waterproof housing having a free end with a transparent window. A photodetector is positioned within the housing at the free end and generates an output signal corresponding to the intensity of light from a light source leaving the egg. The photodetector is shielded from direct light from the light source via a replaceable bumper removably secured to the housing free end. A processor is disposed within the housing and is configured to process output signals from the photodetector to identify cyclical variations in light intensity, wherein a cyclical variation in light intensity indicates the existence of an embryo pulse. In some embodiments of the present invention, the processor processes output signals from the photodetector to identify non-cyclical variations in light intensity, wherein non-cyclical variations in light intensity indicate embryo movement.

According to further embodiments of the present invention, a method of candling eggs includes contacting an egg with a free end of a detector tool, wherein a bumper is secured to the detector tool free end; illuminating the egg with visible light within a range of between 600 nm and 740 nm via a light source; detecting intensity of light leaving the egg via a photodetector within the detector tool, wherein the photodetector is shielded from direct light from the light source via the bumper; generating an output signal that corresponds to detected light intensity; and processing the output signal to identify cyclical and/or non-cyclical variations in light intensity, wherein cyclical variations in light intensity indicate the existence of an embryo pulse, and wherein non-cyclical variations in light intensity indicate embryo movement.

DETAILED DESCRIPTION

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise. All publications, patent applications, patents, and other references mentioned herein are incorporated herein by reference in their entireties.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of "over" and "under". The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

It will be understood that, although the terms "first", "second", etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a "first" element, component, region, layer or section discussed below could also be termed a "second" element, component, region, layer or section without departing from the teachings of the present invention. The sequence of operations (or steps) is not limited to the order presented in the claims or figures unless specifically indicated otherwise.

Methods and apparatus according to embodiments of the present invention may be utilized for accurately identifying live and non-live eggs at any time during embryonic development (also referred to as the incubation period). Embodiments of the present invention are not limited to identification only at a particular day (e.g., day eleven) or time period during the embryonic development period. In addition, methods and apparatus according to embodiments of the present invention may be used with any types of avian eggs including, but not limited to, chicken, turkey, duck, geese, quail, pheasant eggs, exotic bird eggs, etc.

As would be understood by one skilled in the art, eggs are incubated and processed within a carrier, such as an egg flat. Flats may contain any number of rows, such as seven rows of eggs, with rows of six and seven being most common. Moreover, eggs in adjacent rows may be parallel to one another, as in a "rectangular" flat, or may be in a staggered relationship, as in an "offset" flat. Examples of suitable commercial flats include, but are not limited to, the "CHICKMASTER 54" flat, the "JAMESWAY 42" flat and the "JAMESWAY 84" flat (in each case, the number indicates the number of eggs carried by the flat). Egg flats are well known to those of skill in the art and need not be described further herein. The terms "flat" and "carrier" are intended to be used interchangeably herein.

Figure 1:
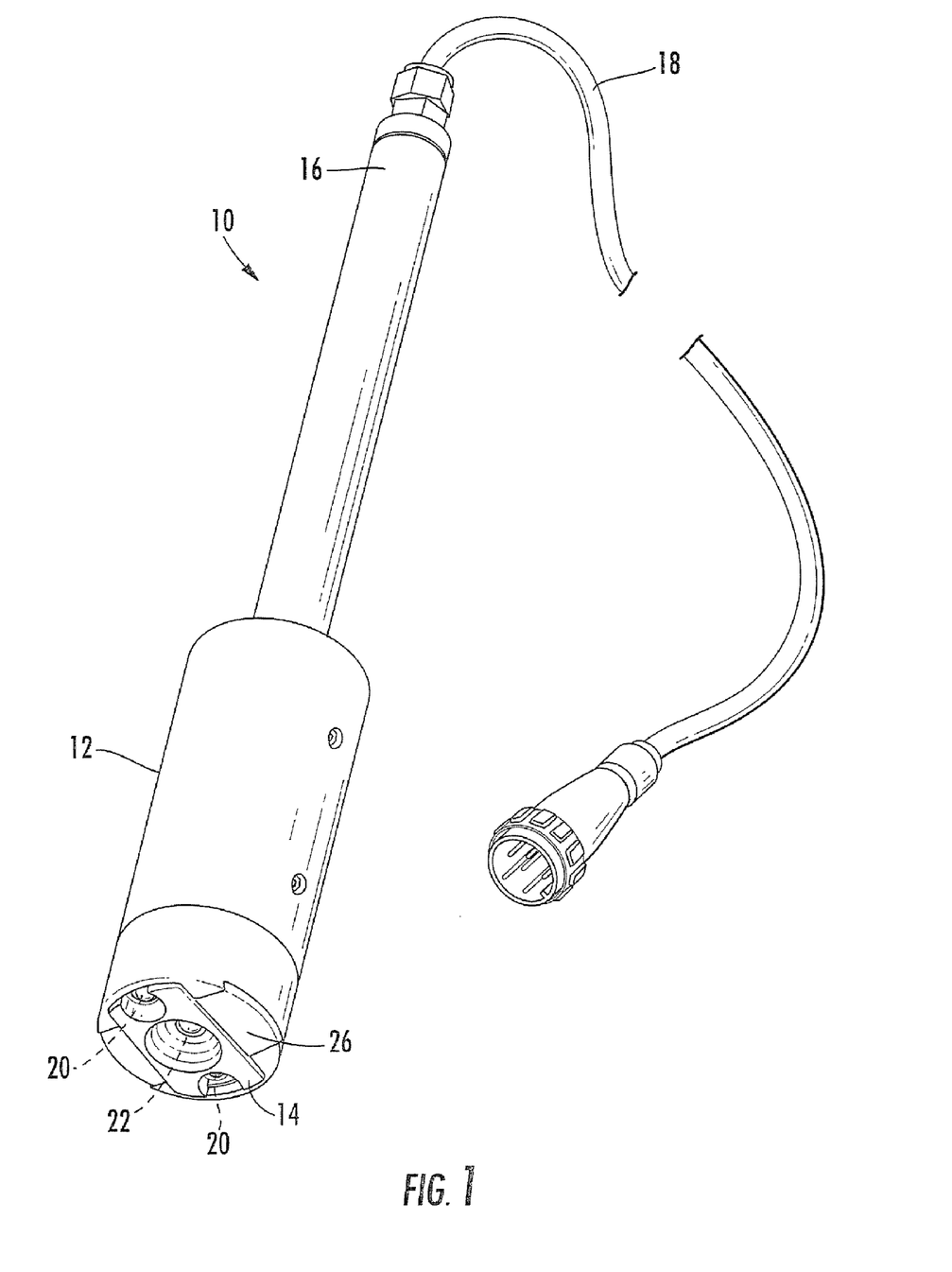
FIG. 1 is a perspective view of a detector tool, according to some embodiments of the present invention.

Referring now to FIG. 1, a detector tool 10 for use in candling eggs, according to some embodiments of the present invention, is illustrated. The illustrated detector tool 10 is configured for use in an automated candling apparatus such as, but not limited to, the Egg Remover® system from Embrex, Inc., Durham, N.C. In operation, a plurality of the detector tools 10, arranged in an array, are utilized to candle a respective array of eggs supported by an egg carrier, as would be understood by those skilled in the art of the present invention.

The illustrated detector tool 10 includes a substantially waterproof housing 12 with a proximal free end 14 and an elongated distal end 16. As will be described below, the free end 14 is configured to be positioned in contacting relationship with an egg. The distal end 16 is attached to a frame that raises and lowers the detector tool 10 relative to a carrier containing eggs. Extending from the distal end 16 of the housing 12 is an electrical cable 18 containing wiring that connects the various electrical components contained within the detector tool 10 with a controller and/or other electrical components of a candling apparatus, as would be understood by those skilled in the art of the present invention. Embodiments of the present invention are not limited to the illustrated configuration of the detector tool housing 12. The detector tool housing 12 may have various shapes, sizes and configurations without limitation. The waterproof housing 12 protects sensitive electronic components disposed therein from liquids, moisture, and debris that may be encountered during candling.

An array of the detector tools 10 are supported in a generally vertical orientation via a frame or other supporting member of a candling apparatus. Conventionally, the frame is movable between a raised position and a lowered position. However, individual detector tools 10 may be configured to be lowered and raised relative to an egg independent of other detector tools in an array. When in the lowered position, each detector tool 10 rests on top of a respective egg 5, as would be understood by those skilled in the art of the present invention.

Disposed within the housing 12 are a pair of light sources 20. Each light source 20 is configured to emit visible light from the housing free end and illuminate an egg positioned adjacent to the housing free end, as will be described below. Also disposed within the housing is a photodetector 22 that is configured to receive light passing through an egg from the light sources 20 during candling. The photodetector 22 generates an output signal corresponding to the intensity of the light leaving an egg. The photodetector 22 may be any type of detector capable of detecting the wavelength(s) of light emitted by the light sources 20.

In the illustrated embodiment, the photodetector 22 is positioned between the pair of light sources 20. However, embodiments of the present invention are not limited to the illustrated configuration of the light sources 20 and photodetector 22. Various orientations of the light sources 20 and photodetector 22 may be utilized as long as the photodetector is shielded from indirect light from external sources and from direct light from the light sources 20, as described below. Moreover, although a pair of light detectors 20 are utilized in the illustrated embodiment, a single light source may be utilized in some embodiments and more than two light sources may be utilized in other embodiments. In addition, more than one photodetector 22 may be utilized in accordance with other embodiments of the present invention.

The pair of light sources 20 are configured to illuminate an egg with visible light. For example, in some embodiments of the present invention, the pair of light sources 20 are light emitting diodes (LEDs) that are configured to emit light from the visible portion of the spectrum. However, embodiments of the present invention are not limited to the use of LEDs. Various types of light sources may be utilized without limitation. Moreover, optical fibers and light pipes may be utilized to provide light from a remotely-located visible light source.

Each light source 20 is configured to emit visible light. For example, in some embodiments, each light source 20 emits light within a range of between about 600 nanometers (nm) and 740 nm. In other embodiments, each light source 20 is configured to emit light within a range of between about 610 nm and 720 nm. Applicants have found that LEDs with center wavelengths (peak intensity) of 625 nm, 639 nm, 660 nm, and 695 nm are particularly effective in detecting the existence of an avian embryo pulse.

Exemplary light sources 20 that may be utilized are the following LED models which are available from Digi-Key Corporation, Thief River Falls, Minn.: 516-1367-ND, 160-1625-ND and 404-1104-ND, with respective central wavelengths of 625 nm, 639 nm and 660 nm. Another light source 20 that may be utilized is the following LED model which is available from Roithner LaserTechnik, Vienna, Austria: ELD 700-524-3 with a central wavelength of 695 nm.

Figure 2A:
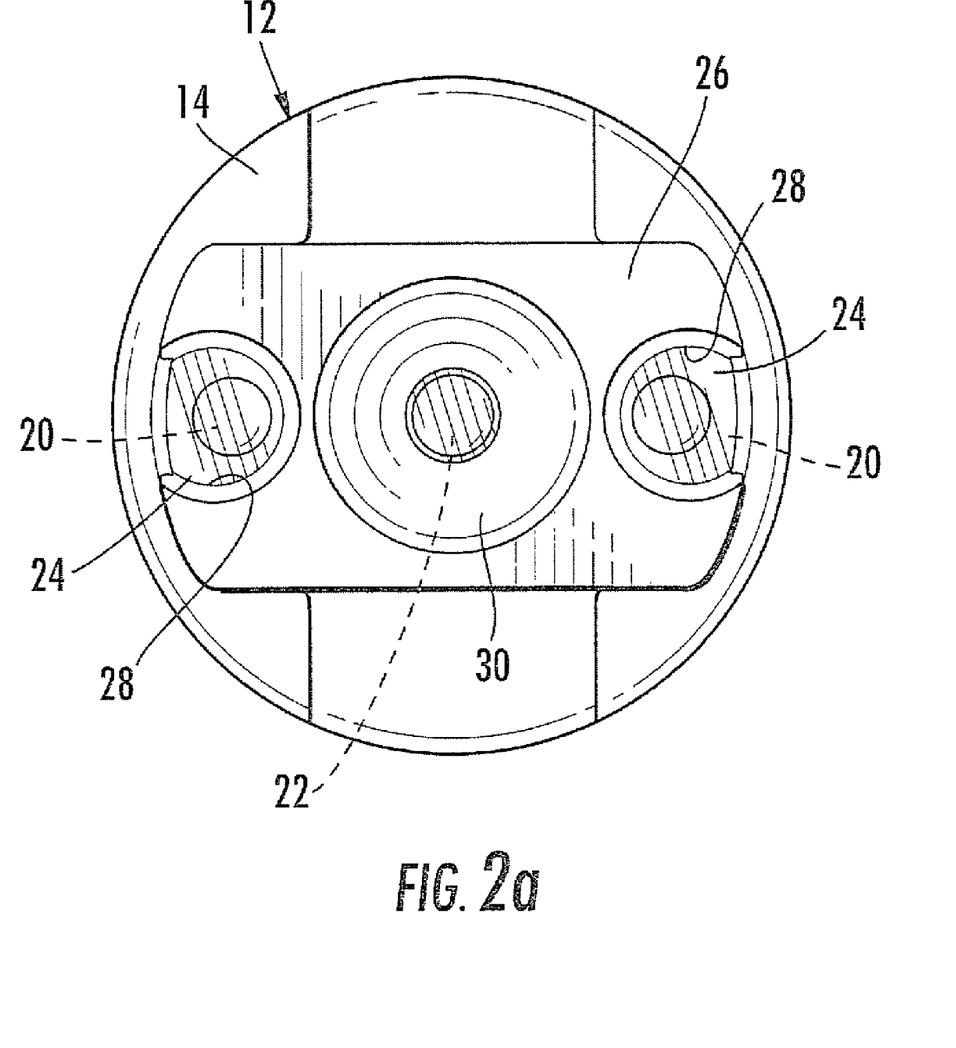
FIG. 2a illustrates the free end of the detector tool of FIG. 1 with the replaceable bumper removably secured thereto.
Figure 2B:
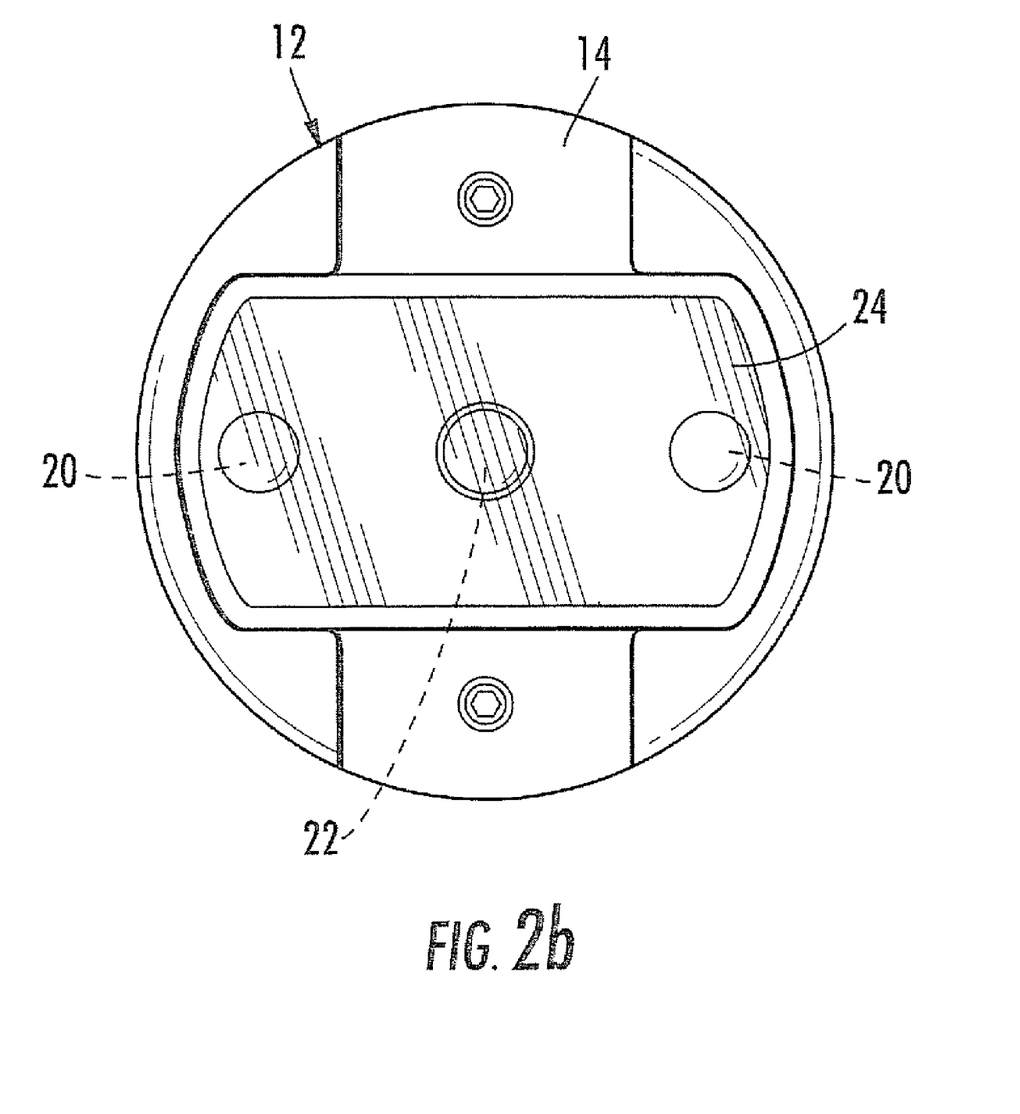
FIG. 2b illustrates the free end of the detector tool of FIG. 1 with the replaceable bumper removed from the free end.

As illustrated in FIGS. 2a-2b, the housing free end 14 includes a transparent window 24 that permits light to pass therethrough. The transparent window may be formed from various types of material, without limitation. Exemplary materials include, but are not limited to, glass, sapphire, and plastic (e.g., non-reflecting, transparent plastic, etc.). As illustrated in FIG. 2b, the pair of light sources 20 are disposed within the housing and emit light through the window 24, and the photodetector 22 is disposed within the housing and receives light leaving an egg through the window 24. The window 24 may be secured to the housing free end 14 in various ways to ensure that the housing remains substantially waterproof.

Figure 3:
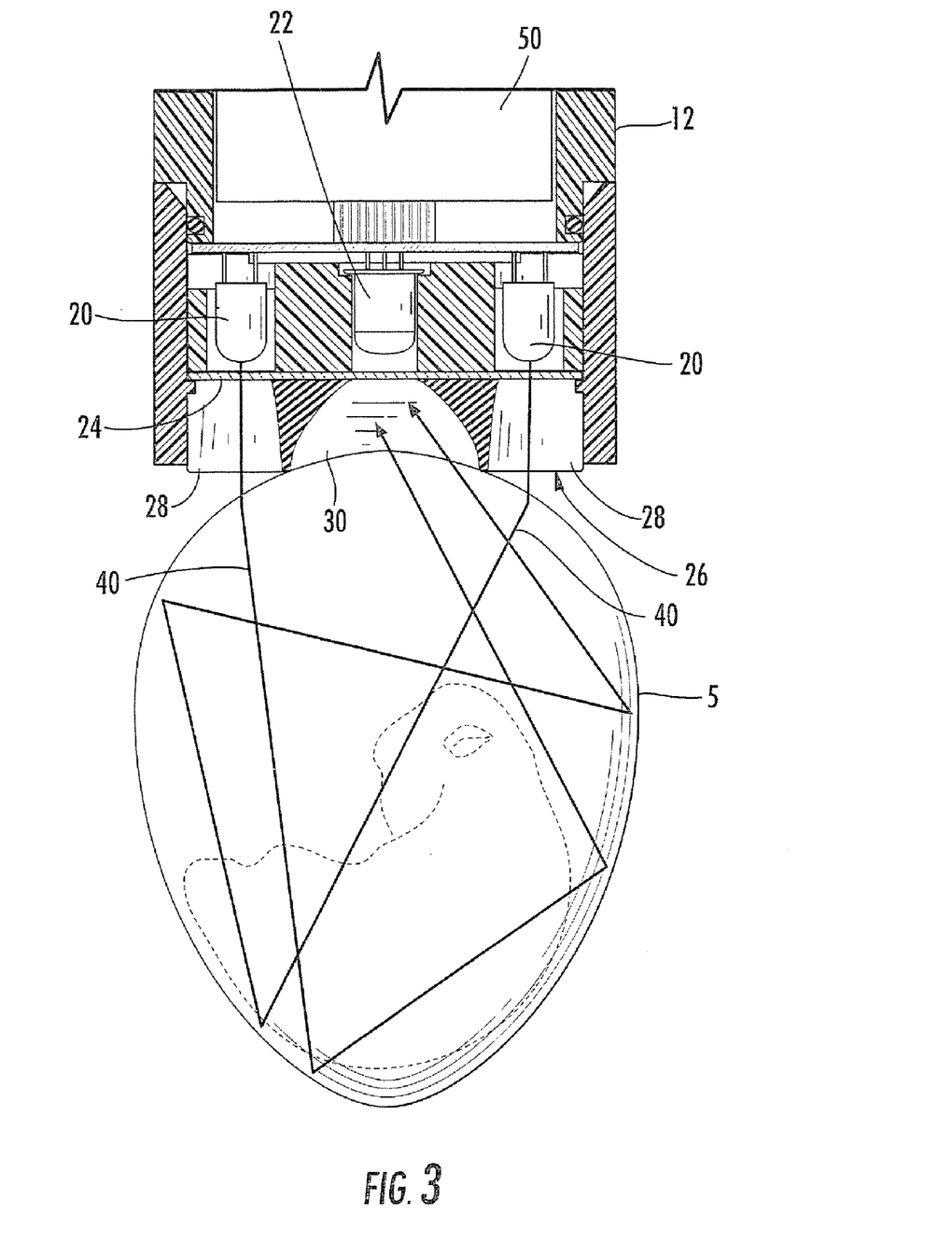
FIG. 3 is a side, cross-sectional view of the free end of the detector tool of FIG. 1, illustrating the replaceable bumper in contact with an egg and illustrating the pair of light sources and the photodetector disposed within the housing behind the transparent window.

A replaceable bumper 26 is secured to the housing free end 14 and is configured to engage an egg in contacting relation therewith when the detector tool 10 is lowered onto the egg 5 (FIG. 3). In some embodiments, the bumper is formed from a compliant material, such as rubber or other resilient material, in order to cushion contact with an egg. An exemplary material includes, but is not limited to, silicone, rubber, etc. with a dark (e.g., black, etc.) colorant. In other embodiments of the present invention, the bumper may be formed from a rigid material. The bumper 26 may have any of various shapes and sizes and is not limited to the illustrated configuration.

The bumper 26 is the only portion of the illustrated detector tool 10 that makes contact with an egg. In some embodiments, the bumper 26 is removably secured to the housing free end 14 to facilitate cleaning and/or replacement thereof. The bumper 26 may be removably secured to the housing free end 14 in various ways, without limitation. For example, the housing free end 14 may have dovetail-shaped slots formed therein that are configured to receive correspondingly dovetail-shaped edge portions of the bumper 26. In other embodiments, the bumper 26 may be removably secured to the housing free end 14 via clips, magnets, adhesives, and/or via various other known methods.

The bumper 26 shields the photodetector 22 from stray light (e.g., light from an external source, etc.) and from direct light from the light sources 20. In other words, the bumper 26 shields the photodetector 22 from a straight light path from the light source. However, indirect light paths through the egg are allowed, as shown in FIG. 3. As illustrated in FIGS. 2a and 3, the bumper 26 includes a pair of apertures 28 through which the pair of light sources 20 emit light. The illustrated apertures 28 each have a configuration that causes them to act as respective shields for the light sources 20 such that light emitted by each light source 20 is directed into an egg contacting the bumper 26. The illustrated bumper 26 also includes an aperture 30 that surrounds the photodetector 22 and shields the photodetector 22 from stray light and from direct light from the light sources 20. The portion of the egg shell within the aperture 30 is in the shadow of light emitted by an external source. Embodiments of the present invention are not limited to the illustrated shape and configuration of the bumper or of the apertures 28, 30. A replaceable bumper 26 may have various shapes and configurations that serve the function of shielding a photodetector 22, according to embodiments of the present invention.

Photodetector shielding aperture 30 is configured to overlie a portion of an egg 5 in contacting relationship therewith when the detector tool 10 is lowered such that the bumper contacts an egg 5. The illustrated aperture 30 has a generally hemispherical shape that facilitates stable engagement of the detector tool 10 with an egg. However, embodiments of the present invention are not limited to the illustrated shape and configuration of aperture 30. In some embodiments, the weight of the detector tool 10 is sufficient to seat the bumper 26 on an egg 5 such that stray light cannot enter the aperture 30 and reach the photodetector 22.

In operation and once the detector tool 10 is positioned adjacent to an egg 5, the light sources 20 emit visible light (indicated as 40 in FIG. 3) into the egg 5. The photodetector 22 receives light that leaves the egg 5 and generates an output signal corresponding to the intensity of the light leaving the egg. According to some embodiments of the present invention, the photodetector 22 may be provided with an integral amplifier to limit environmental electrical noise (e.g., 60 Hz from power lines). According to some embodiments of the present invention, a filter may be utilized to block wavelengths other than wavelengths emitted by the light sources 20. For example, if the light sources 20 emit red light (e.g., 660 nm), then a reduction in sensitivity to non-red light, such as blue and green external light (e.g., from mercury vapor lighting, fluorescent lighting, etc.), can be achieved with a photodetector 22 having a filter that blocks blue (450 nm-490 nm) and green (490 nm-560 nm) light. An exemplary filter for blocking blue and green light is a J43-942 red filter, available from Edmund Optics, Inc., Barrington, N.J. Amplifiers and filters are well known to those skilled in the art and need not be described further herein.

A processor 50 disposed within the housing is in communication with the photodetector 22 and processes output signals from the photodetector to determine the viability of an egg 5. Eggs having an embryo pulse and/or movement may be designated as live eggs. Viability may be determined by processing the output signal to determine the existence of cyclical variations in light intensity that correspond to an embryo pulse. Viability may be determined by processing the output signal to determine the existence of non-cyclical variations in light intensity that correspond to embryo movement. In addition, viability may be determined by processing the output signal to determine the existence of both cyclical and non-cyclical variations in light intensity.

In addition to sensing variations in light level, the photodetector 22 may provide an average light level in an egg that can be used to provide other important information about egg conditions. For example, the average light reflected to the photodetector 22 from a clear egg will be greater than the average light reflected from a live Day 18 egg because the broad beam of light from the light source that impinges upon the side of the egg will reflect throughout the egg rather than being absorbed by a large embryo. Similarly, the average light reaching the photodetector 22 from an upside down egg will be less than that from a normally positioned egg (blunt end up) because more of the embryo is available to block the light. These effects may be enhanced by using a light source having a different wavelength than a light source that is optimal for detecting heartbeat. If multiple light sources with multiple wavelengths are used, then their outputs may be time multiplexed to allow sensing of each wavelength or light source separately with the single photodetector 22.

Figure 4:
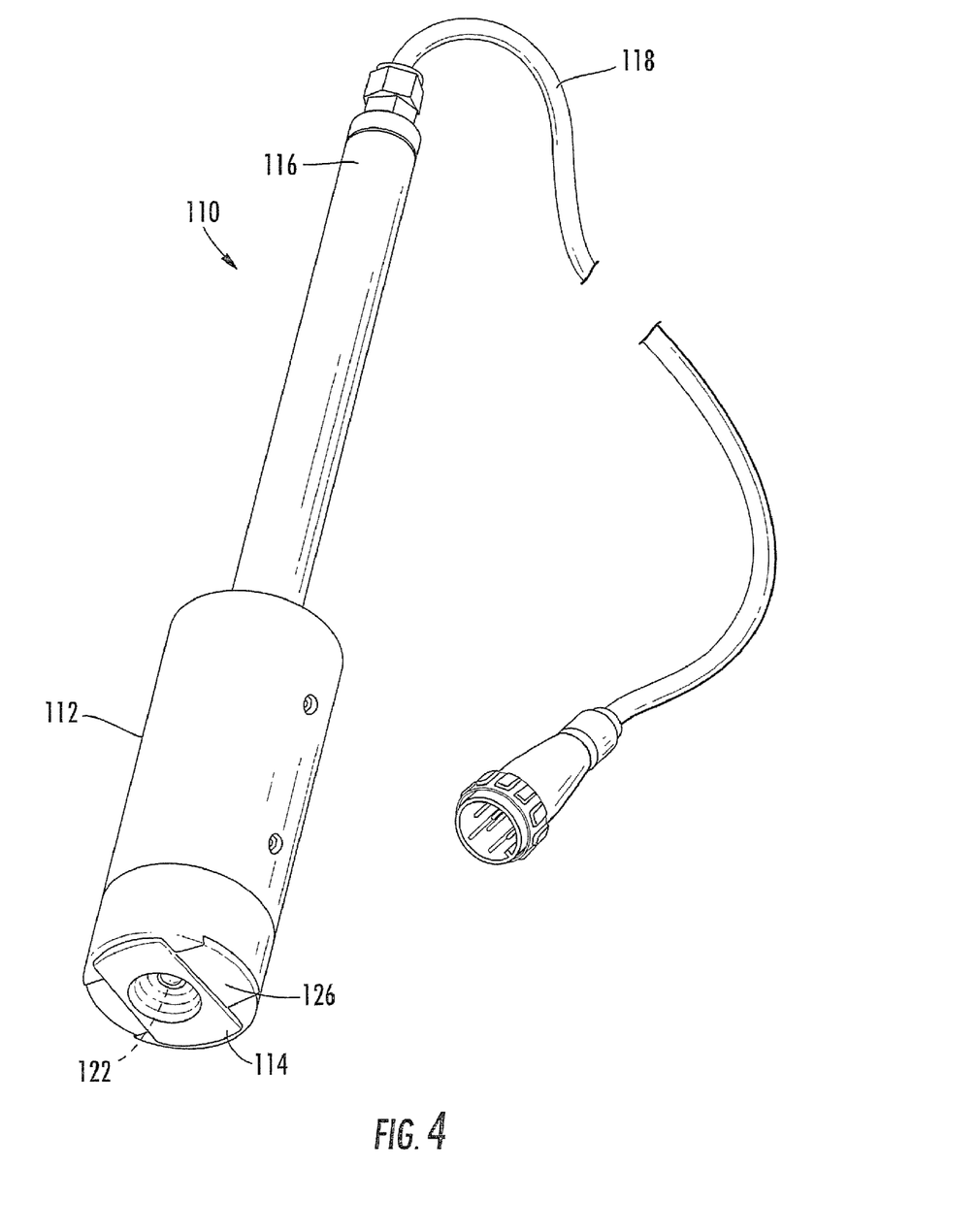
FIG. 4 is a perspective view of a detector tool, according to other embodiments of the present invention.

Referring now to FIG. 4, a detector tool 110 for use in candling eggs, according to other embodiments of the present invention, is illustrated. The illustrated detector tool 110 includes a substantially waterproof housing 112 with a proximal free end 114 and an elongated distal end 116. The free end 114 is configured to be positioned in contacting relationship with an egg. The distal end 116 is attached to a frame that raises and lowers the detector tool 110 relative to a carrier containing eggs, as described above. Extending from the distal end 116 of the housing 112 is an electrical cable 118 containing wiring that connects the various electrical components contained within the detector tool 110 with a controller and/or other electrical components of a candling apparatus, as would be understood by those skilled in the art of the present invention.

Disposed within the housing 112 is a photodetector 122 that is configured to receive light passing through an egg from one or more external light sources during candling. As described above, the photodetector 122 generates an output signal corresponding to the intensity of the light leaving an egg. The photodetector 122 may be any type of detector capable of detecting the wavelength(s) of light emitted by a light source.

Figure 5A:
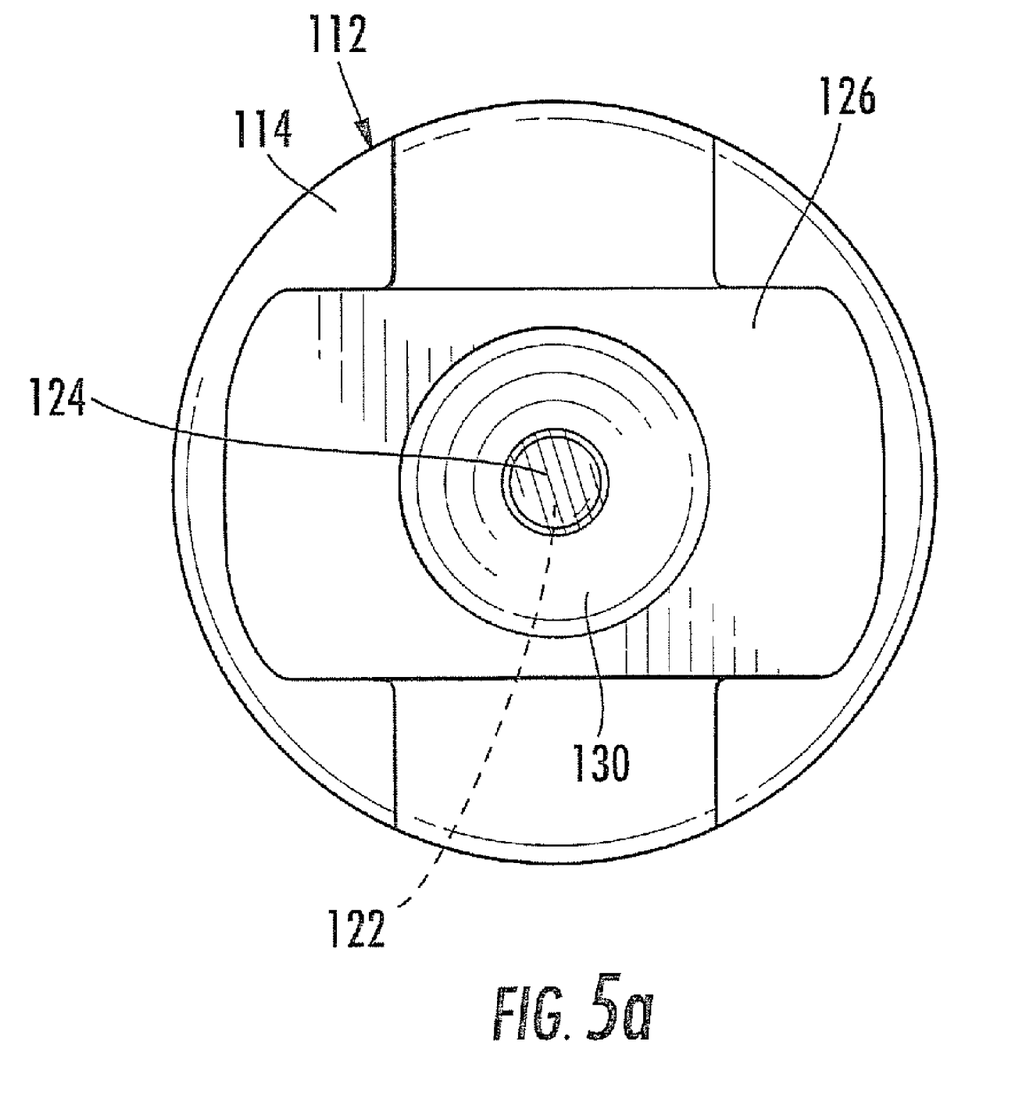
FIG. 5a illustrates the free end of the detector tool of FIG. 4 with the replaceable bumper removably secured thereto.
Figure 5B:
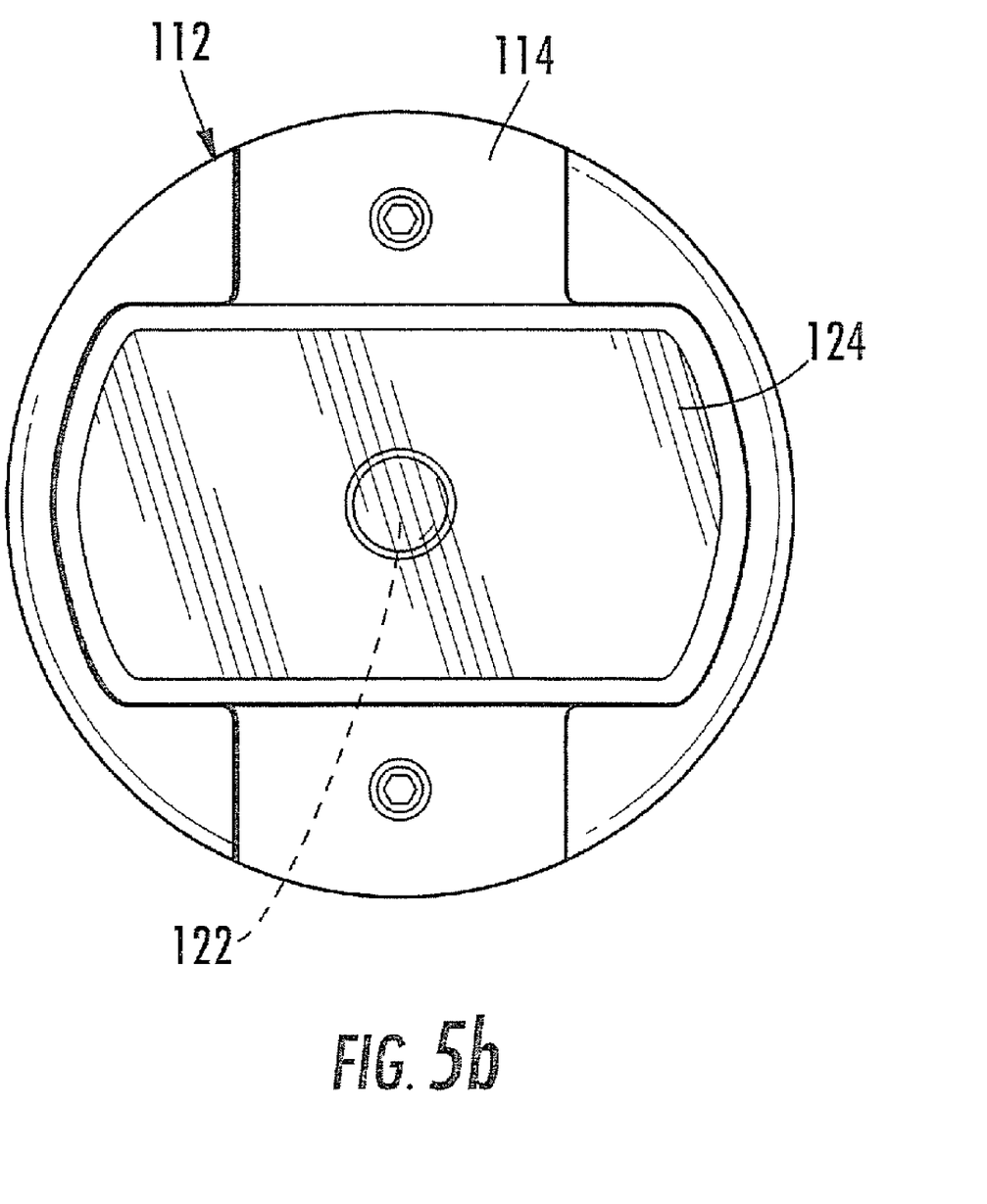
FIG. 5b illustrates the free end of the detector tool of FIG. 4 with the replaceable bumper removed from the free end.

As illustrated in FIGS. 5a-5b, the housing free end 114 includes a transparent window 124 that permits light to pass therethrough. The photodetector 122 is disposed within the housing and receives light leaving an egg through the window 124. The window 124 may be secured to the housing free end 114 in various ways to ensure that the housing remains substantially waterproof.

Figure 6:
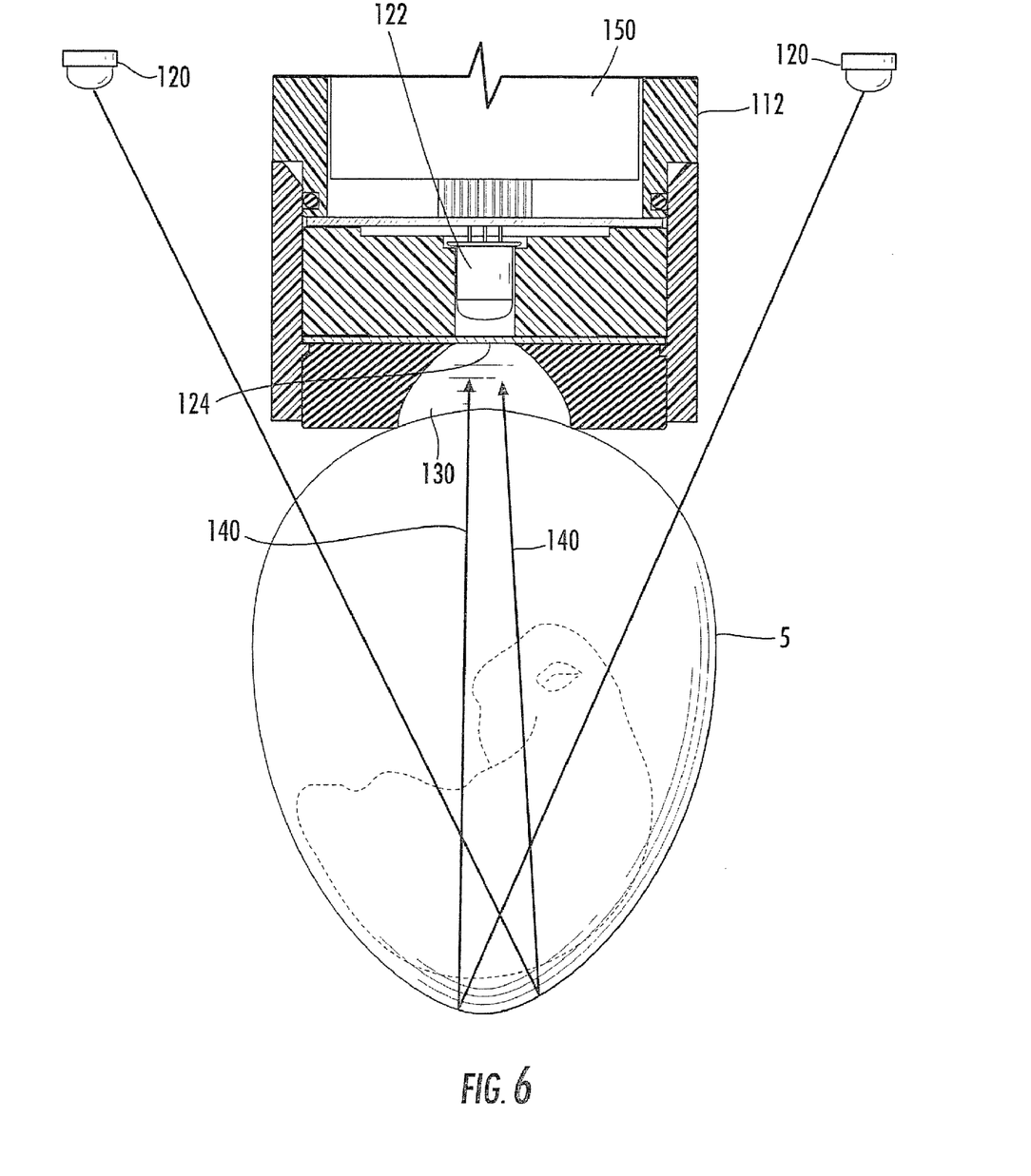
FIG. 6 is a side, cross-sectional view of the free end of the detector tool of FIG. 4, illustrating the replaceable bumper in contact with an egg and illustrating the photodetector disposed within the housing behind the transparent window.

A replaceable bumper 126 is secured to the housing free end 114 and is configured to engage an egg in contacting relation therewith when the detector tool 110 is lowered onto the egg 5 (FIG. 6). As described above, in some embodiments the bumper is formed from a compliant material, such as rubber or other resilient material, in order to cushion contact with an egg. In other embodiments of the present invention, the bumper 126 may be formed from a rigid material. The bumper 126 may have any of various shapes and sizes and is not limited to the illustrated configuration.

As described above, the bumper 126 is the only portion of the illustrated detector tool 110 that makes contact with an egg. In some embodiments, the bumper 126 is removably secured to the housing free end 114 to facilitate cleaning and/or replacement thereof. The bumper 126 may be removably secured to the housing free end 114 in various ways, without limitation. For example, the housing free end 114 may have dovetail-shaped slots formed therein that are configured to receive correspondingly dovetail-shaped edge portions of the bumper 126. In other embodiments, the bumper 126 may be removably secured to the housing free end 114 via clips, magnets, adhesives, and/or via various other known methods.

The bumper 126 shields the photodetector 122 from stray light (e.g., light from an external source, etc.) and from direct light from the light sources 120. The illustrated bumper 126 includes an aperture 130 that surrounds the photodetector 122 and shields the photodetector 122 from stray light and from direct light from the light sources 120. The portion of the egg shell within the aperture 130 is in the shadow of light emitted by an external source. Embodiments of the present invention are not limited to the illustrated shape and configuration of the bumper or of the aperture 130. A replaceable bumper 126 may have various shapes and configurations that serve the function of shielding a photodetector 122, according to embodiments of the present invention.

The photodetector shielding aperture 130 is configured to overlie a portion of an egg 5 in contacting relationship therewith when the detector tool 110 is lowered such that the bumper contacts an egg 5. The illustrated aperture 130 has a generally hemispherical shape that facilitates stable engagement of the detector tool 110 with an egg. However, embodiments of the present invention are not limited to the illustrated shape and configuration of aperture 130.

In operation, and once the detector tool 110 is positioned adjacent to an egg 5, one or more external light sources 120 emit visible light (indicated as 140 in FIG. 6) into the egg 5. The photodetector 122 receives light that leaves the egg 5 and generates an output signal corresponding to the intensity of the light leaving the egg. As described above, the photodetector 122 may be provided with an integral amplifier to limit environmental electrical noise, and/or a filter to block wavelengths other than wavelengths emitted by the light sources 120. A processor 150 disposed within the housing is in communication with the photodetector 122 and processes output signals from the photodetector to determine the viability of an egg 5.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed is:

1. An apparatus for candling eggs, comprising:
   a housing having a free end;
   at least one light source configured to emit visible light from the housing free end and illuminate an egg positioned adjacent to the housing free end, wherein the at least one light source emits visible light within a range of between 600 nm and 740 nm;
   a photodetector disposed at the housing free end and configured to generate an output signal corresponding to intensity of light from the at least one light source leaving the egg, the photodetector being shielded from external light and from direct light from the at least one light source, the photodetector being oriented in a parallel arrangement with the at least one light source for receiving light emitted therefrom;
   a bumper operably engaged with the housing free end, the bumper being configured to engage an egg in contacting relation therewith, and the bumper defining a first aperture through which the at least one light source emits light and a second aperture through which the photodetector receives light; and
   a processor configured to identify cyclical variations in light intensity using the output signal, wherein a cyclical variation in light intensity indicates the existence of an embryo pulse.

2. The apparatus of claim 1, wherein the housing free end comprises a transparent window, wherein the at least one light source is disposed within the housing and emits light through the window, and wherein the photodetector is disposed within the housing and receives light leaving an egg through the window.

3. The apparatus of claim 1, wherein the bumper shields the photodetector from direct light from the at least one light source.

4. The apparatus of claim 1, wherein the at least one light source emits visible light within a range of between 610 nm and 720 nm.

5. The apparatus of claim 1, wherein the at least one light source comprises a light emitting diode (LED) configured to emit visible light with a peak intensity at one of the following wavelengths: 625 nm, 639 nm, 660 nm, and 695 nm.

6. The apparatus of claim 1, wherein at least one light source and the photodetector are disposed within the housing.

7. The apparatus of claim 1, wherein at least one light source comprises a pair of light sources.

8. The apparatus of claim 1, wherein the processor is disposed within the housing.

9. The apparatus of claim 8, wherein the processor is configured to identify non-cyclical variations in light intensity using the output signal, wherein non-cyclical variations in light intensity indicate embryo movement.

10. An apparatus for candling eggs, comprising:
    a housing having a single free end;
    a pair of light sources disposed within the housing, each light source being configured to emit visible light from the housing free end and illuminate an egg positioned adjacent to the housing free end, and wherein each light source emits visible light within a range of between 600 nm and 740 nm;
    a photodetector positioned at the housing free end between the pair of light sources, the photodetector being configured to generate an output signal corresponding to intensity of light from the light sources leaving the egg, the photodetector being shielded from external light and from direct light from the light sources, the photodetector being oriented in a parallel arrangement with the pair of light sources for receiving light emitted therefrom;
    a bumper operably engaged with the housing free end, the bumper being configured to engage an egg in contacting relation therewith, and the bumper defining a first aperture through which one of the pair of light sources emits light, a second aperture through which the other of the pair of light sources emits light, and a third aperture through which the photodetector receives light; and
    a processor disposed within the housing and in communication with the photodetector, the processor being configured to identify cyclical variations in light intensity using the output signal, wherein a cyclical variation in light intensity indicates the existence of an embryo pulse.

11. The apparatus of claim 10, wherein the processor is configured to identify non-cyclical variations in light intensity using the output signal, wherein non-cyclical variations in light intensity indicate embryo movement.

12. The apparatus of claim 10, wherein the bumper shields the photodetector from direct light from the pair of light sources.

13. The apparatus of claim 10, wherein the housing free end comprises a transparent window, wherein the pair of light sources emit light through the window, and wherein the photodetector receives light leaving an egg through the window.

14. The apparatus of claim 10, wherein the pair of light sources are configured to illuminate an egg with light from one or more selected portions of a spectrum.

15. The apparatus of claim 10, wherein each light source emits visible light within a range of between 610 nm and 720 nm.

16. The apparatus of claim 10, wherein each light source comprises a light emitting diode (LED) configured to emit visible light with a peak intensity at one of the following wavelengths: 625 nm, 639 nm, 660 nm, and 695 nm.

17. The apparatus of claim 10, wherein the photodetector is positioned between the pair of light sources.

18. A method of candling eggs, comprising:
    positioning an egg adjacent a bumper operably engaged with a single free end of a detector tool, wherein the free end has at least one light source and a photodetector oriented in a parallel arrangement with the at least one light source for receiving light emitted therefrom, the bumper defining a first aperture through which the at least one light source emits light and a second aperture through which the photodetector receives light;
    illuminating the egg with visible light within a range of between 600 nm and 740 nm from the free end via the at least one light source;
    detecting intensity of light leaving the egg via the photodetector, wherein the photodetector is shielded from external light and from direct light from the at least one light source;
    generating an output signal that corresponds to detected light intensity; and
    processing the output signal to identify at least one of cyclical and non-cyclical variations in light intensity, wherein cyclical variations in light intensity indicate the existence of an embryo pulse, and wherein non-cyclical variations in light intensity indicate embryo movement.

19. The method of claim 18, wherein illuminating the egg with visible light comprises illuminating the egg with visible light within a range of between 610 nm and 720 nm.

20. The method of claim 18, wherein the at least one light source comprises a light emitting diode (LED) configured to emit visible light with a peak intensity at one of the following wavelengths: 625 nm, 639 nm, 660 nm, and 695 nm.

21. A method of candling eggs, comprising:
    contacting an egg with a single free end of a detector tool, wherein a bumper is secured to the detector tool free end, and wherein the detector tool has a photodetector oriented in a parallel arrangement with at least one light source for receiving light emitted therefrom, the bumper defining an aperture through which the photodetector receives light;
    illuminating the egg with visible light from the at least one light source, wherein the at least one light source emits visible light within a range of between 600 nm and 740 nm;
    detecting intensity of light leaving the egg via the photodetector, wherein the photodetector is shielded from direct light from the at least one light source via the bumper;
    generating an output signal that corresponds to detected light intensity; and
    processing the output signal to identify at least one of cyclical and non-cyclical variations in light intensity, wherein cyclical variations in light intensity indicate the existence of an embryo pulse, and wherein non-cyclical variations in light intensity indicate embryo movement.

22. An apparatus for candling eggs, comprising:
    a housing having a free end;
    at least one light source configured to emit visible light from the housing free end and illuminate an egg positioned adjacent to the housing free end, wherein the at least one light source emits visible light within a range of between 600 nm and 740 nm;
    a photodetector disposed at the housing free end and configured to generate an output signal corresponding to intensity of light from the at least one light source exiting the egg, the photodetector being shielded from external light and from direct light from the at least one light source, and the photodetector being oriented in a parallel arrangement with the at least one light source such that visible light from the at least one light source is emitted substantially parallel to an axis of the photodetector defined by the orientation thereof for receiving the emitted visible light; and
    a processor configured to identify cyclical variations in light intensity using the output signal, wherein a cyclical variation in light intensity indicates the existence of an embryo pulse.

23. The apparatus of claim 22, wherein the at least one light source and the photodetector are adjacently disposed within respective apertures defined by the housing at the free end.

24. An apparatus for candling eggs, comprising:
    a housing having a free end;
    at least one light source configured to emit visible light from the housing free end and illuminate an egg positioned adjacent to the housing free end;
    a photodetector disposed at the housing free end and configured to generate an output signal coffesponding to intensity of light from the at least one light source exiting the egg, the photodetector being shielded from external light and from direct light from the at least one light source, and the photodetector being oriented in a parallel arrangement with the at least one light source such that light from the at least one light source is emitted substantially parallel to an axis of the photodetector defined by the orientation thereof for receiving the emitted light; and
    a processor configured to identify cyclical variations in light intensity using the output signal, wherein a cyclical variation in light intensity indicates the existence of an 25. The apparatus of claim 24, wherein the at least one light source and the photodetector are adjacently disposed within respective apertures defined by the housing at the free end.

26. The apparatus of claim 24, wherein the at least one light source is configured to emit visible light.

27. An apparatus for candling eggs, comprising:
    a housing having a free end;
    at least one light source configured to emit light from the housing free end and illuminate an egg positioned adjacent to the housing free end;
    a photodetector disposed at the housing free end and configured to generate an output signal coffesponding to intensity of light from the at least one light source leaving the egg, the photodetector being shielded from external light and from direct light from the at least one light source, the photodetector being oriented in a parallel arrangement with the at least one light source for receiving light emitted therefrom;
    a bumper operably engaged with the housing free end, the bumper being configured to engage an egg in contacting relation therewith, and the bumper defining a first aperture through which the at least one light source emits light and a second aperture through which the photodetector receives light; and
    a processor configured to identify cyclical variations in light intensity using the output signal, wherein a cyclical variation in light intensity indicates the existence of an embryo pulse.

28. A method of candling eggs, comprising:
    positioning an egg adjacent a bumper operably engaged with a single free end of a detector tool, wherein the free end has at least one light source and a photodetector oriented in a parallel arrangement with the at least one light source for receiving light emitted therefrom, the bumper defining a first aperture through which the at least one light source emits light and a second aperture through which the photodetector receives light;
    illuminating the egg with light from the free end via the at least one light source;
    detecting intensity of light leaving the egg via the photodetector, wherein the photodetector is shielded from external light and from direct light from the at least one light source;
    generating an output signal that conesponds to detected light intensity; and
    processing the output signal to identify at least one of cyclical and non-cyclical variations in light intensity, wherein cyclical variations in light intensity indicate the existence of an embryo pulse, and wherein non-cyclical variations in light intensity indicate embryo movement.

* * * * *

UNITED STATES PATENT AND TRADEMARK OFFICE
CERTIFICATE OF CORRECTION

| | | |
|---|---|---|
| PATENT NO. | : 8,107,060 B2 | Page 1 of 1 |
| APPLICATION NO. | : 11/947225 | |
| DATED | : January 31, 2012 | |
| INVENTOR(S) | : John H. Hebrank and Daniel L. Kennedy | |

It is certified that error appears in the above-identified patent and that said Letters Patent is hereby corrected as shown below:

In the Claims

Column 13, line 61, Claim 24, cancel the text beginning with "24. An apparatus for candling" to and ending "existence of an" in column 14, line 14, and insert the following claim:

--24. An apparatus for candling eggs, comprising: a housing having a free end; at least one light source configured to emit light from the housing free end and illuminate an egg positioned adjacent to the housing free end; a photodetector disposed at the housing free end and configured to generate an output signal corresponding to intensity of light from the at least one light source exiting the egg, the photodetector being shielded from external light and from direct light from the at least one light source, and the photodetector being oriented in a parallel arrangement with the at least one light source such that light from the at least one light source is emitted substantially parallel to an axis of the photodetector defined by the orientation thereof for receiving the emitted light; and a processor configured to identify cyclical variations in light intensity using the output signal, wherein a cyclical variation in light intensity indicates the existence of an embryo pulse.--

Signed and Sealed this
Twenty-fourth Day of February, 2015

Michelle K. Lee
*Deputy Director of the United States Patent and Trademark Office*